US00PP10483P

United States Patent [19]

Holtkamp, Sr.

[11] Patent Number: Plant 10,483

[45] Date of Patent: Jul. 7, 1998

[54] AFRICAN VIOLET PLANT NAMED CENTENNIAL

[75] Inventor: Reinhold Holtkamp, Sr., Rees-Haffen, Germany

[73] Assignee: International Plant Breeding A.G., Bern, Switzerland

[21] Appl. No.: 798,297

[22] Filed: Feb. 7, 1997

[51] Int. Cl.[6] ..... A01H 5/00

[52] U.S. Cl. ..... Plt./69.1

[58] Field of Search ..... Plt./69.1

*Primary Examiner*—James R. Feyrer

*Assistant Examiner*—Melissa L. Kimball

*Attorney, Agent, or Firm*—Foley & Lardner

[57] ABSTRACT

A new and distinct cultivar of African violet named Centennial, as described and illustrated, and particularly characterized by its large, star-shaped, very light pink flowers with somewhat darker centers and slightly wavy edges; strong, upright flower stems that curve slightly toward the center to form a compact bouquet above the leaves; medium green, heart-shaped leaves; profuse flowering; vigorous and compact growth habit; flowering 9–10 weeks after potting, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Centennial.

The new cultivar was referred to during the breeding and selection process by the designation 911/25 and is a product of a planned breeding program. The new cultivar was originated from a cross made by me in the controlled breeding program in Haffen, Federal Republic of Germany. The female, or seed parent was a cultivar designated 911 star. The male, or pollen parent was a cultivar designated 925 star.

Centennial was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Centennial has not been observed under all possible environmental conditions. The phenotype may vary significantly with variations in environment such as temperature, light intensity and day length. The following observations, measurements and values describe the new cultivar as grown in Haffen, West Germany, and Nashville, Tenn. under greenhouse conditions which closely approximate those generally used in commercial practice.

The following traits have been repeatedly observed and are determined to be basic characteristics of Centennial, which in combination distinguish this african violet as a new and distinct cultivar:

1) Strong, upright flower stems curving slightly toward the center.

2) Large, star-shaped, very light pink flowers with wavy edges.

3) Profuse flowering.

4) Each plant carries 8–10 and more upright flower stems each of which carries 8–10 and more flowers.

5) Long lasting, non-dropping flowers.

6) Vigorous and compact grower.

7) Plant saleable 9 to 10 weeks after potting.

8) Seed capsules push slightly through.

9) Medium green, heart-shaped leaves.

10) After maturity the flowers dry off, and remain on the peduncle without becoming infected by botrytis.

The new cultivar is most similar to Corinna, disclosed in

U.S. Plant Pat. No. 6,534. Similarities are the shape and color of the flowers. Both are star-shaped and are in the Red Group 56. However, Corinna has darker, evenly colored blooms whereas Centennial has lighter blooms with a somewhat darker center.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 12 p.m. in Nashville, Tenn.

Botanical classification: *Saintpaulia ionantha*, Ramat., c.v. Centennial.

Parentage:

*Male parent.*—911 star.

*Female parent.*—925 star.

Propagation: The new cultivar holds its distinguishing characteristics through successive propagations by leaf cuttings.

Plant: From 9 cm to 11 cm tall when grown in pots, and 24–28 cm in diameter when fully grown.

*Leaves.*—General form: Heart-shaped. Diameter: 50–60 mm wide and 65–75 mm long. Texture: Velvety. Aspect: Hairy, slightly serrated, slightly shiny. Veins: Upperside: visible; underside: well pronounced, light green to purplish red, shiny. Color (upperside): Yellow-green group 147 A. Color (underside): Greyed-purple group 186 A with patches of greyed-green group 194 C. Petiole: Strong, green with purplish brown touch, hairy.

*Flowers.*—Buds: Bell-shaped, light green, 5–7 mm just before opening. Sepals: Five (5). Color: Purplish brown. Calyx: Shape: Funnel-shaped. Aspect: Spear-shaped, hairy. Peduncle: Character: Strong, upright, hairy. Color: Purplish brown. Individual flowers: Size: 50–55 mm. Shape: Star-shaped (5 petals of equal size). Color (upperside): Red group 56 C to D with center being 56 A to B. Under cooler temperatures and more intensive lighting, the light pink tends to intensify. Color (underside): Red group 56 D. Borne: Each flower stem carries 8–10 and more flowers on strong, upright peduncles that are free standing above the leaves, thereby forming a compact bouquet. Flowering habit: Flowers 9–10 weeks after potting.

*Reproductive organs.*—Stamens: Five (5). Anthers: 5 composed of 10 anther cells, seed capsules push slightly through. Filaments: Yellowish white, 3–4 mm long. Pollen Color: Yellow Group 7 A. Styles: 6–7 mm long, light pink, base of ovary light green and hairy. Roots: Normally developed, white when young, turning slightly brownish when older.

Disease resistance: Up to date, Centennial has shown very good resistance to all major violet diseases.

General observations: Centennial is an attractive cultivar due to its large, star-shaped, very light pink flowers with somewhat darker center contrasting nicely with the bright yellow anthers. The petals are slightly wavy and sometimes an additional very small petal may develop in the center. A tight bouquet of flowers free standing above the leaves develops 9–10 weeks after potting. Each of the 8–10 and more strong flower stems carries 8–10 and more flowers. Medium green, heart-shaped leaves surround the flower bouquet. The flowres are long-lasting and non-dropping and the seed capsules push slightly through.

I claim:

1. A new and distinct cultivar of African violet plant named Centennial, as described and illustrated, and particularly characterized by its large, star-shaped, very light pink flowers with somewhat darker centers and slightly wavy edges; strong, upright flower stems that curve slightly toward the center to form a compact bouquet above the leaves; medium green, heart-shaped leaves; profuse flowering; vigorous and compact growth habit; flowering 9–10 weeks after potting, and by its long lasting and non-dropping flowers.

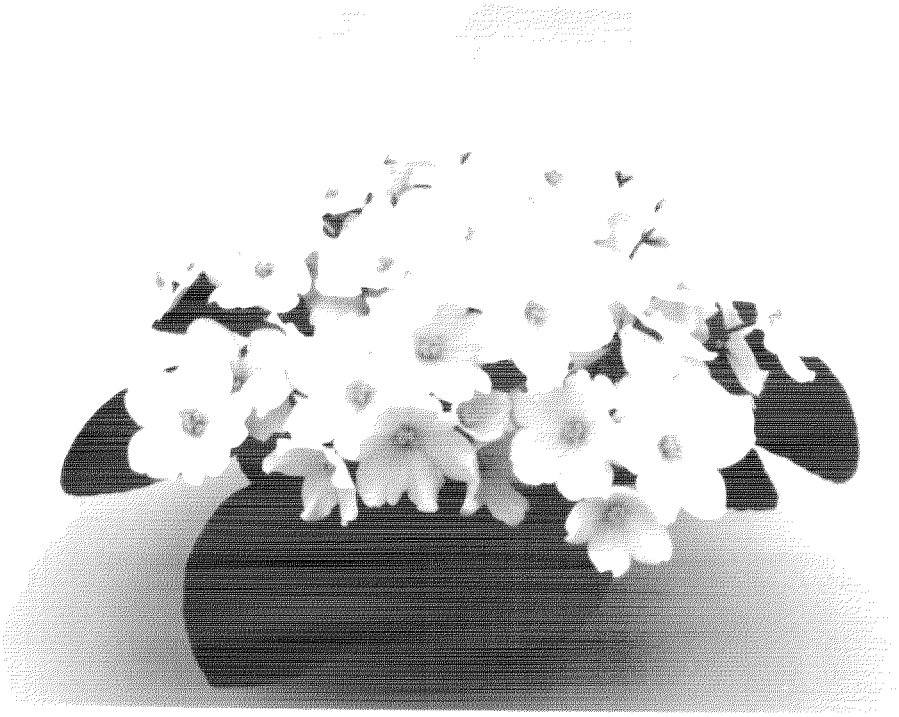

* * * * *